United States Patent [19]

Schroeppel

[11] Patent Number: 4,770,177
[45] Date of Patent: Sep. 13, 1988

[54] APPARATUS AND METHOD FOR ADJUSTING HEART/PACER RELATIVE TO CHANGES IN VENOUS DIAMETER DURING EXERCISE TO OBTAIN A REQUIRED CARDIAC OUTPUT.

[75] Inventor: Edward A. Schroeppel, Miramar, Fla.

[73] Assignee: Telectronics N.V., Netherlands, Netherlands Antilles

[21] Appl. No.: 830,089

[22] Filed: Feb. 18, 1986

[51] Int. Cl.⁴ ............................................. A61N 1/36
[52] U.S. Cl. ............................. 128/419 PG; 128/670; 128/786
[58] Field of Search ............ 128/419 P, 419 PG, 663, 128/670, 672, 673, 687, 691, 692, 694, 695, 713, 774, 782, 784, 786

[56] References Cited

U.S. PATENT DOCUMENTS

| | | |
|---|---|---|
| 2,634,721 | 5/1951 | Greenwood, Jr. ................. 128/2.05 |
| 2,976,865 | 3/1961 | Shipley ............................. 128/2.05 |
| 3,038,465 | 6/1962 | Allard et al. ...................... 128/2.05 |
| 3,088,323 | 5/1963 | Welkowitz et al. ................ 73/398 |
| 3,294,988 | 12/1966 | Packard .............................. 310/8 |
| 3,563,245 | 2/1971 | McLean et al. .................... 128/419 |
| 3,614,954 | 10/1971 | Mirowski et al. .................. 128/419 |
| 3,650,277 | 3/1972 | Sjostrand et al. ................. 128/419 C |
| 3,815,611 | 6/1974 | Denniston III .................... 128/782 |
| 3,905,356 | 9/1975 | Fletcher et al. ................... 128/774 |
| 3,906,960 | 9/1975 | Lehr .................................. 128/419 |
| 4,164,939 | 8/1979 | Kolin ................................ 128/692 |
| 4,191,193 | 3/1980 | Seo ................................... 128/675 |
| 4,428,378 | 1/1984 | Anderson et al. ............. 128/419 PG |
| 4,432,372 | 2/1984 | Monroe ............................. 128/675 |
| 4,436,092 | 3/1984 | Cook et al. ........................ 128/419 |
| 4,456,013 | 6/1984 | DeRossi et al. ................... 128/675 |
| 4,503,857 | 3/1985 | Boute et al. ...................... 128/419 |
| 4,525,775 | 6/1985 | Eydelman .......................... 128/672 |
| 4,535,774 | 8/1985 | Olson ................................ 128/419 |
| 4,543,954 | 10/1985 | Cook et al. ........................ 128/419 |
| 4,554,921 | 11/1985 | Boute et al. .................. 128/419 PG |
| 4,562,843 | 1/1986 | Djordjevich et al. .............. 128/672 |
| 4,566,456 | 1/1986 | Koning et al. ..................... 128/419 |
| 4,567,892 | 2/1986 | Plicchi et al. ..................... 128/419 |
| 4,600,017 | 7/1986 | Schroeppel ........................ 128/675 |

OTHER PUBLICATIONS

Myers et al., "IEEE Transactions on Biomedical Engineering" vol. 10, No. 2, Apr. 1963, p. 83.
Nealeigh et al., "ISA Transactions" vol. 19, No. 1, pp. 84–87, 1976.

Primary Examiner—William E. Kamm
Attorney, Agent, or Firm—Thomas R. Vigil; Henry W. Collins

[57] ABSTRACT

The apparatus paces a heart in accordance with the heart/pacer rate needed to produce a required cardiac output while a person is exercising or undergoes emotional stress in response to changes in venous blood vessel diameter. The apparatus includes a pacer adapted to be implanted in a human body and having a pulse generator and control circuitry, which may be realized by a microprocessor, therein; a pacing lead adapted to be implanted in a heart having a tip electrode adapted to engage and supply pacing pulses to a right ventricle of a heart; a piezoelectric sensor for determining changes in diameter of a vein in the human body; and computing circuitry including the control circuitry, for relating the changes in venous blood vessel diameter with the required pacing rate needed to supply a desired cardiac output and for causing the pacer to pace the heart at the required rate when the heart is not naturally paced.

18 Claims, 3 Drawing Sheets

APPARATUS AND METHOD FOR ADJUSTING HEART/PACER RELATIVE TO CHANGES IN VENOUS DIAMETER DURING EXERCISE TO OBTAIN A REQUIRED CARDIAC OUTPUT.

CROSS-REFERENCE TO RELATED APPLICATIONS

This application relates to U.S. application Ser. No. 632,625 filed July 19, 1984 for: PACING LEAD WITH SENSOR, issued to U.S. Pat. No. 4,600,017 on July 15, 1986, and to U.S. application Ser. No. 924,764 filed Oct. 10, 1986, now U.S. Pat. No. 4,730,619 for: APPARATUS AND METHOD FOR ADJUSTING HEART-/PACER RATE RELATIVE TO EJECTION TIME TO OBTAIN A REQUIRED CARDIAC OUTPUT.

BACKGROUND OF THE INVENTION

FIELD OF THE INVENTION

The present invention relates to a pacer system which is adapted to alter the rate of pacing pulses delivered by an artificial pacemaker or pacer to a heart while an individual is exercising, utilizing changes in venous blood vessel diameter brought about by an anticipatory need of the body to increase cardiac output.

Description of the Prior Art

Heretofore patients with heart dysfunctions or heart disease such as sinus node disease have been able to live a relatively normal life with the implantation of an artificial pacemaker often referred to as a pacer. However, such pacers have not always been able to mimic the response of a normal healthy heart. A normal heart responds to exercise and stress by increasing cardiac output through increased heart rate or stroke volume.

In this respect, patients with sinus node disease have lost the ability to increase heart rate with exercise. Accordingly, it has become a goal of optimal pacing to provide exercise responsiveness in a pacer by sensing the need for increased cardiac output.

With a view toward obtaining this goal, a number of pacemakers have been proposed for indirectly sensing the need for increased heart rate by sensing P-waves, nerve impulses, Q-T interval, pH, oxygen saturation, respiratory rate, stroke volume, motion, atrial pressure and temperature.

A P-wave triggered artificial pacemaker adapted to be exercise responsive by responding to average atrial rate has been proposed in the Knudson & Amundson, U.S. Pat. No. 4,313,442.

An artificial pacemaker responsive to changes in the Q-T interval is proposed in the Rickards, U.S. Pat. No. 4,228,803.

The Funke, U.S. Pat. No. 4,312,355 discloses a dual pace-dual sense cardiac pacer which is able to stimulate the atrium and/or the ventricle and which is able to entrain the ventricle, when the atrial rate increases, while preventing bradycardic episodes. The pacer action is triggered by detection of naturally occurring atrial and ventricular action or pulses within a predetermined time period.

The Roline, U.S. Pat. No. 4,363,325 discloses a multiple mode pacer activated to switch modes relative to heart rate thereby preventing atrial bradycardia. This is achieved by mode switching of the pacer from an atrial synchronous mode to a ventricular inhibited mode. A proposal for placing electrodes on Hering's nerve that extends from receptors in the sinus and glomus carotids is disclosed in the Gonzales U.S. Pat. No. 4,201,219.

Sensors for sensing blood pH are proposed in the Alcidi, U.S. Pat. No. 4,009,721 and the Mauer et al, U.S. Pat. No. 4,252,124. Alcidi controls a pacer relative to blood pH.

In the Bornzin, U.S. Pat. No. 4,467,807 molecular oxygen is sensed with an oxygen sensor, preferably of the type as disclosed in the Wirtzfeld et al, U.S. Pat. Nos. 4,202,339 and 4,299,820. The Wirtzfeld et al patents teach measuring of oxygen saturation of blood using optical techniques. The transmittance of light through blood is used by Wirtzfeld et al to measure oxygen concentration. Bornzin teaches using such measurements for controlling the pacing of a heart.

An artificial pacemaker that is adjusted relative to the oxygen saturation in a pacing system where oxygen saturation is sensed at the tip of a catheter in the right ventricle is proposed in the Wirtzfeld et al, U.S. Pat. No. 4,202,339.

Another artificial cardiac pacemaker which increases pacing rate in accordance with an increase in respiration rate is proposed in the Krasner, U.S. Pat. No. 3,593,718.

Pacer systems for adjusting pacing relative to motion or mechanical activity sensed are proposed in the Dahl, U.S. Pat. No. 4,240,132 and the Anderson et al, U.S. Pat. No. 4,428,378.

The Heilman et al., U.S. Pat. No. 4,303,075 discloses a method and apparatus for maximizing stroke volume through AV pacing using an implanted cardioverter/-pacer which is programmed with an AV delay tailored to a particular patient. The mechanism detects and utilizes impedance of the heart measured across two electrodes in contact with heart muscle. See also the Olson, U.S. Pat. No. 4,533,774 which teaches controlling a pacer relative to variations in stroke volume.

The Cohen, U.S. Pat. No. 3,358,690 proposes the sensing of pressure in the right atrium and utilization of the pressure sensed to control pacing of an electrode in the right ventricle.

The Zacouto, U.S. Pat. No. 3,857,399 discloses, in FIG. 19 thereof, a pressure sensor that measures either left ventricular pressure or intramyocardial pressure and apparently uses pressure averages over relatively long periods of time for controlling pacing.

The Sjostrand et al., U.S. Pat. No. 3,650,277 discloses a system for reducing and controlling the blood pressure of a hypertensive patient utilizing pressure sensed in an artery.

Pressure sensors and transducers mounted on catheters are old and well known in the medical arts.

The apparatus and method of the present invention differ from the previously proposed apparatus and methods referred to above by providing a cardiac pacing system which utilizes a pressure sensor mounted in the wall of a pacing lead for measuring changes in venous blood vessel diameter that occur as an anticipatory need for the return of blood to the heart during exercise or emotional stress as anticipated by the human body, and utilizing such changes in venous blood vessel diameter for controlling the pacing during exercise.

SUMMARY OF THE INVENTION

According to the present invention there is provided an apparatus for pacing a heart in accordance with the heart/pacer rate needed to produce a required cardiac output while a person is exercising in response to changes in venous blood vessel diameter. The apparatus comprises a pacer which is adapted to be implanted in a human body and which has a pulse generator and control circuitry which may be realized by a microprocessor therein, a pacing lead which is adapted to be implanted in a heart and which has a tip electrode adapted to engage and supply pacing pulses to a right ventricle of a heart, a sensor for determining changes in diameter of a vein in the human body, and processing circuitry, including the control circuitry, for relating the changes in venous blood vessel diameter with the required pacing rate needed to supply a desired cardiac output and for causing the pacer to pace the heart at the required rate when the heart is not naturally paced.

Further according to the invention, there is provided a method for pacing a heart in accordance with the heart rate needed to produce a required cardiac output while the person is exercising in response to changes in venous blood vessel diameter, comprising the steps of determining changes in the diameter of a vein; relating the changes in venous blood vessel diameter with the required heart rate needed to supply a desired cardiac output; and pacing the heart at the required heart rate when the heart is not naturally paced.

Alternatively, the method and apparatus can be used in conjunction with another sensing system such as a sensing system which senses blood pressure, ejection time, $pO_2$, $pCO_2$ or another parameter.

A pacing system using a sensor for detecting changes in venous blood vessel diameter in conjunction with another type of sensor for sensing changes in blood pressure, ejection time, $pO_2$, $pCO_2$ or some other parameter can provide assurance to the pacing system that the body is about to demand a more rapid heart rate.

DESCRIPTION OF THE PREFERRED EMBODIMENT

Figure 1:
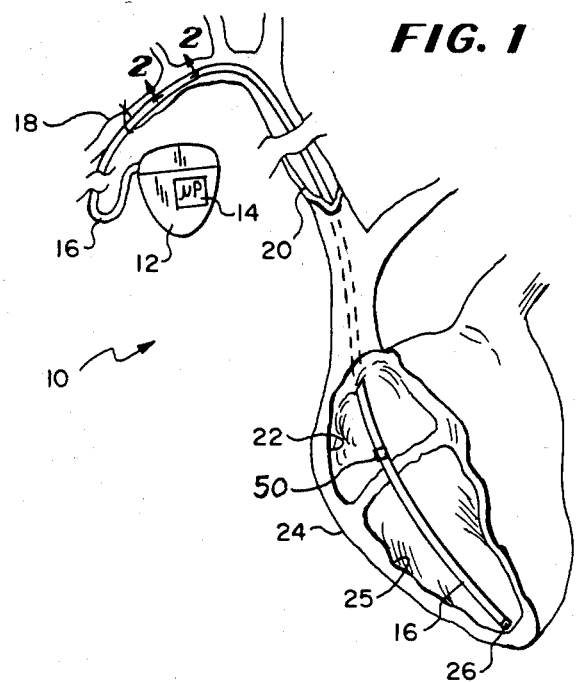
FIG. 1 is a fragmentary plan view of a cardiac pacing system showing a cardiac pacer, a lead extending through a vein to the right ventricle of a heart, and a sensor mounted on the lead in a location so as to be situated in the vein.

Referring now to the drawings in greater detail, there is illustrated therein a pacing system 10 constructed according to the teachings of the present invention which includes a pacer 12 having a microprocessor 14 therein, a pacing lead 16 which extends from the pacer 12 through a vein 18 which connects with the superior vena cava 20 leading to the right atrium 22 of a heart 24. The lead 16 extends through the right atrium and into the right ventricle 25 where a tip electrode 26 of the lead 16 is positioned adjacent the apex of the right ventricle 25.

Although the pacing system 10 is shown as being a single chamber unipolar system, it is to be understood that it could be a bipolar system or a dual chamber unipolar or bipolar system.

In accordance with the teachings of the present invention, a portion 30 of the lead 16 which is adapted to be received in a portion 32 of the vein 18 has a sensor 34 mounted in the body 36 of the lead 16 so as to be exposed to or be positioned on the outer cylindrical surface 38 of the lead body 36.

The sensor 34 can be of any conventional type and is preferably a piezoelectric or bimorph type sensor 34 which can be made very thin. A pair of conductors 41 and 42 are mounted in the wall of the lead body 36 and connected between the piezoelectric sensor 34 and the pacer 12 for providing electrical signals when a pressure or force is exerted upon the sensor 34 such as the force of the contracting vein 18.

Also, in the unipolar lead 16 illustrated in the FIGS., the lead body 16 has mounted therein a coiled conductor 44 (or multiple conductors which are connected in parallel) that extends between the tip electrode 26 and the pacer 12 for transmitting electrical signals picked up by the tip electrode 26 or for supplying electrical pulses from the pacer 12 to the tip electrode 26.

As a result of exercise, stress or emotion, a decrease in $pO_2$ and increase in $pCO_2$ in the blood will occur. Also, a change in pH can occur. Such changes result from the increased metabolism in the body and such changes are not anticipatory in nature.

However, cardiovascular changes appear in the body in anticipation of a behavior. In this respect, immediately prior to or during the early stages of exercise, stress or emotion, the sympathetic nervous system acts to constrict the lumen of central, visceral and peripheral veins, such as vein 18 which can be a cephalic, external jugular, or other vein on either the right or left side of the body.

This constriction increases venous return of blood to the heart 24. Such increased venous return brings about an increase in atrial and ventricular contractions (heart rate) resulting in an increased cardiac output (cardiac output = heart rate x stroke volume).

Also, this sympathetic neural component of regulating heart rate is independent of the fluid conduction system of the heart or the electrical stimulation system for stimulating the heart and is anticipatory of a need, i.e. a need for increased cardiac output.

Figure 2:
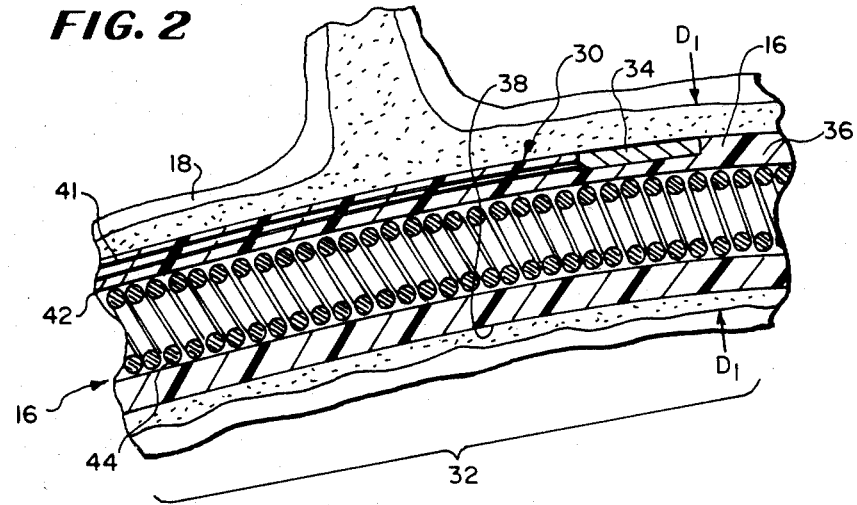
FIG. 2 is an enlarged sectional view of the portion of the vein containing the lead and sensor when the patient is in a relaxed state.
Figure 3:
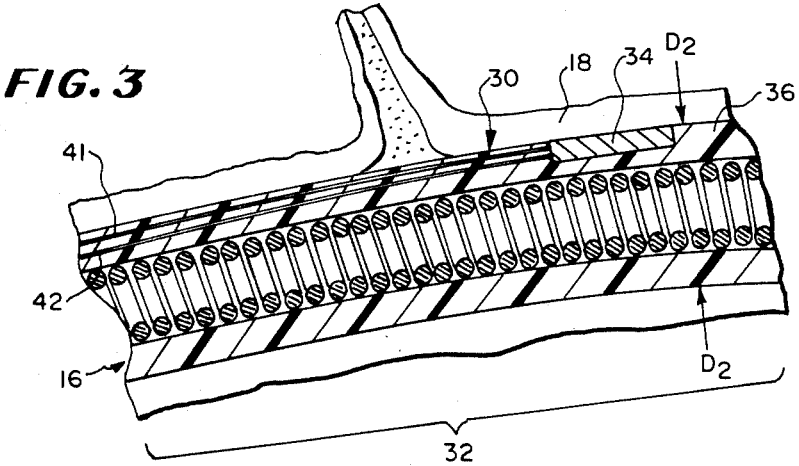
FIG. 3 is a sectional view similar to the view shown in FIG. 2 but shows the vein when the patient is in a state of beginning to exercise.

According to the teachings of the present invention, the rate of pacing is controlled by the microprocessor 14 in the pacer 12 relative to changes in the diameter of the vein 18 so that a closed loop cardiac pacing system is provided with the sensor 34, the pacer 12 and the tip electrode 26. As shown in FIG. 2 the vein 18 is shown in a relaxed non-constricted or dilated state with an inner diameter $D_1$. With the vein 18 in this state, no pressure is exerted on the pressure sensor 34 and accordingly, no signal is transmitted from the sensor to the cardiac pacer 12.

However, when a need is anticipated by the sympathetic nervous system, the wall of the vein 18 is contracted and constricted so as to exert pressure on the sensor 34. A change of potential generated by the deformation of the piezoelectric sensor 34 is transmitted to the cardiac pacer 12 by the wire conductors 41 and 42.

It is to be noted that the piezoelectric sensor 34 is used to detect the force of the constricting vein 18 and not blood pressure.

The amount of change in the diameter of the venous blood vessel 18 is indicative of the anticipated need for increased cardiac output and the electrical signals generated by the piezoelectric sensor 34 and transmitted to the cardiac pacer 12 indicate to the microprocessor 14 that a change in the rate of stimulation of the heart is required.

The changes in the rate of stimulation relative to changes in the diameter of the vein 18 are controlled by a program or algorithm stored in the microprocessor 14.

Figure 4:
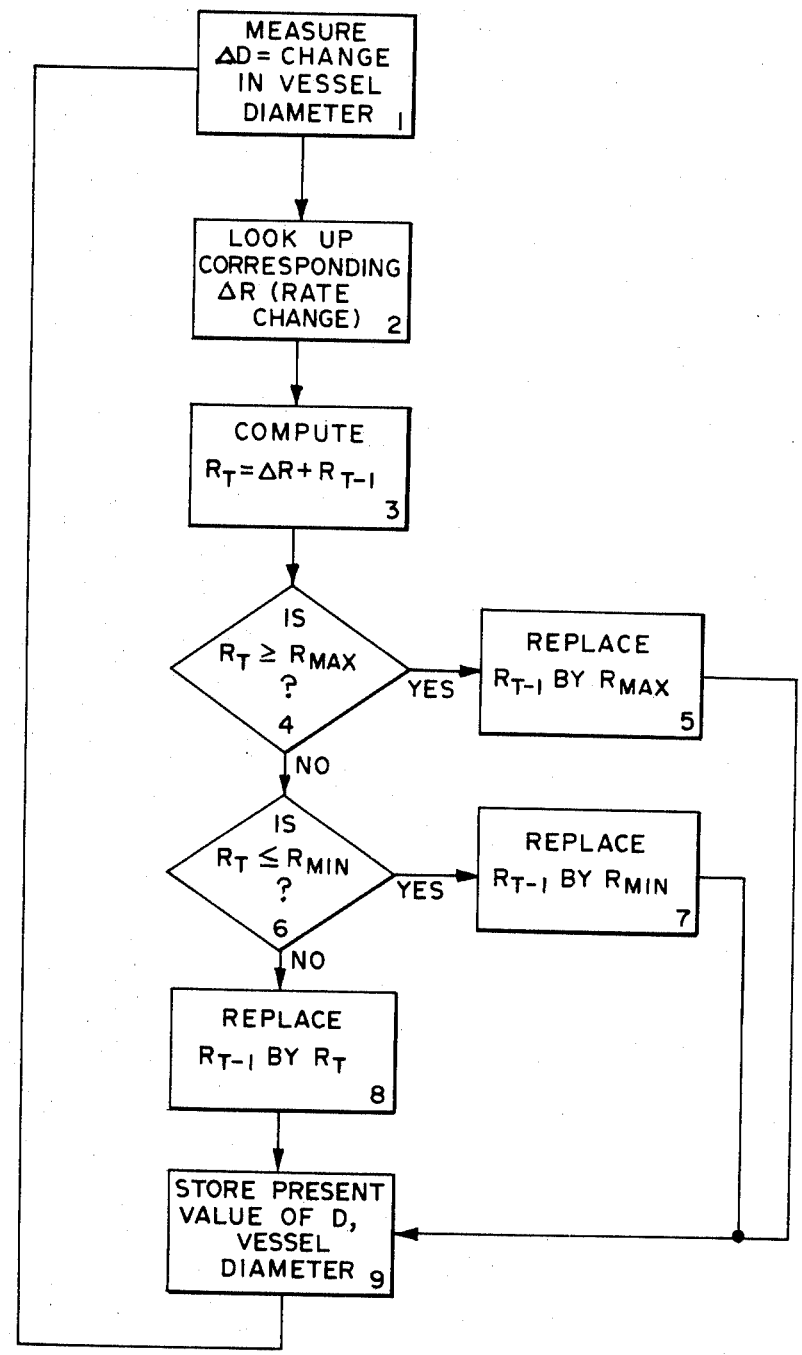
FIG. 4 is a flow chart of the program or routine carried out by the control circuitry (e.g. microprocessor) of the apparatus shown in FIG. 1.

The steps carried out by the program or routine for controlling changes in the rate of stimulation relative to changes in the venous blood vessel diameter are shown in FIG. 4 and can be defined as follows:

STEP 1. Here the changes in blood vessel diameter relative to measurements of blood vessel diameter are calculated.

STEP 2. Here the microprocessor makes use of the calculated change in blood vessel diameter to determine the appropriate change in rate of stimulation relative to the change in blood vessel diameter as determined from a lookup table of such values.

STEP 3. Here the rate $R_T$ is calculated. The rate $R_T$ is the rate at which the cardiac pacer should stimulate the heart based upon the change in rate and the existing rate.

STEP 4. At STEP 4, the newly calculated value for the rate $R_T$ is compared to a programmed maximum rate $R_{MAX}$ at which the cardiac pacer 12 can stimulate the heart. If the cardiac pacer 12 is operating at its programmed maximum rate, the prior rate is replaced by the programmed maximum rate at STEP 5 and the program loops to STEP 9 where the venous blood vessel diameter value is stored in the memory of the microprocessor 14 for comparative purposes.

STEP 5. If the newly determined rate $R_T$ is at or above the programmed maximum rate, the programmed maximum rate replaces the prior rate.

STEP 6. If the newly determined rate $R_T$ is not at the programmed maximum rate of the cardiac pacer 12, the new value of the rate $R_T$ is compared to the programmed mimimum rate $R_{MIN}$ at which the cardiac pacer 12 can stimulate the heart. If the cardiac pacer 12 is operating at its programmed minimum rate, and the newly determined rate is at or less than the programmed minimum rate, the prior rate is replaced by the programmed minimum rate at STEP 7 and the program loops to STEP 9 for storing of the present blood vessel diameter in the memory of the microprocessor 14 for comparative purposes.

STEP 7. If the newly determined rate $R_T$ is less than or equal to the programmed minimum rate, then the prior rate is replaced by programmed minimum rate.

STEP 8. If the newly determined or calculated rate $R_T$ is between the maximum rate and the minimum rate, then the program replaces the previously calculated rate $R_{T-1}$ with the newly calculated rate $R_T$.

STEP 9. At this step, the present value of the blood vessel diameter is stored in the memory of the microprocessor 14.

In the program represented by the flow chart shown in FIG. 4, the pacer rate changes, $\Delta R_T$, may be smoothed by smoothing the changes in venous blood vessel diameter, $\Delta D_T$. This can be done in several ways.

One approach is to compute the sign (positive or negative) of the result of $\Delta D = D_T - (D_{T-1})$ when $D_T$ is measured and compare the sig (positive or negative) to the sign of the N−1 previously computed differences which have been stored in the memory. If no sign change has occurred in N consecutive samples, the algorithm then proceeds to determine the appropriate rate change.

Figure 5:
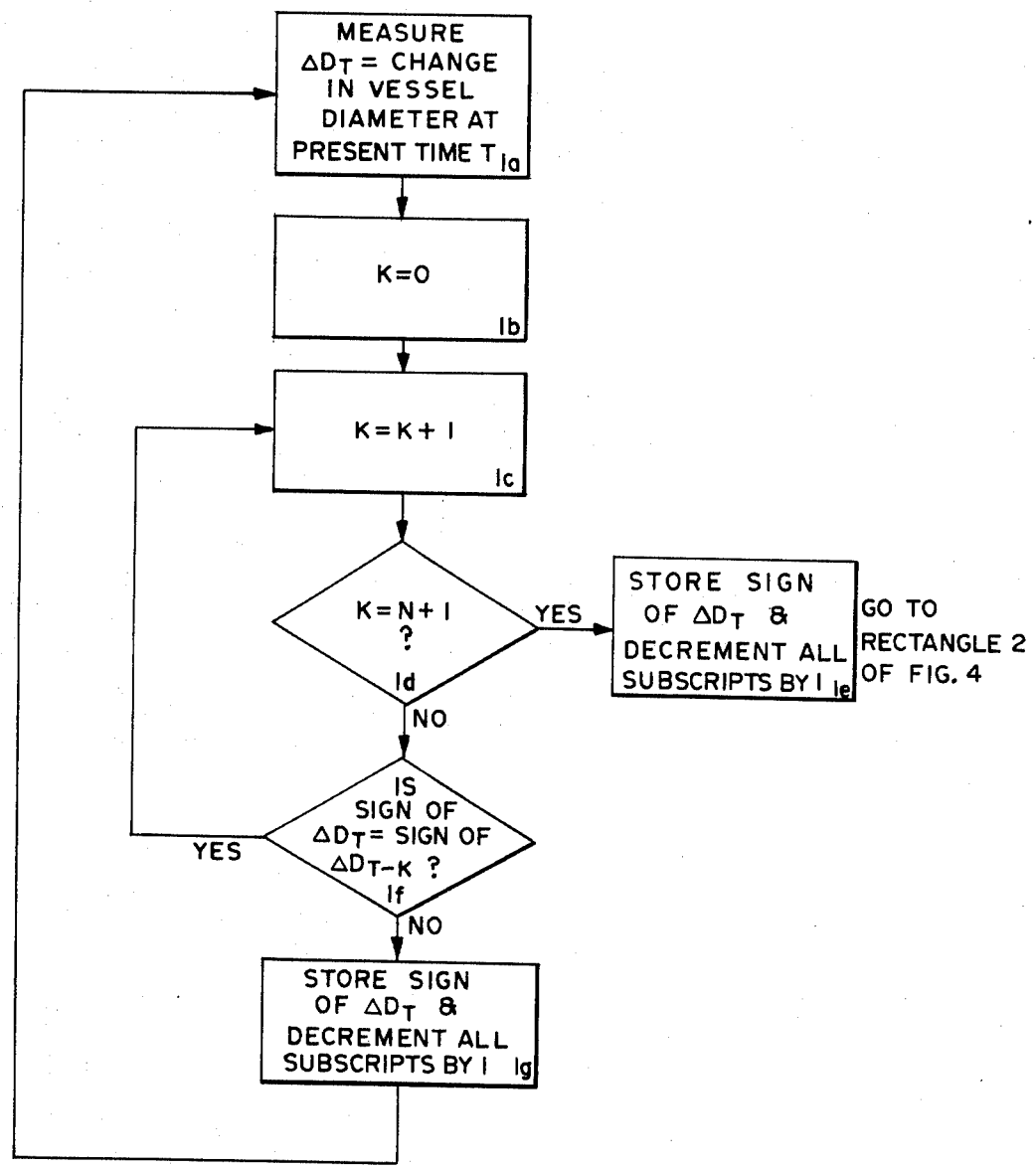
FIG. 5 is a flow chart of a subroutine that can be carried out by the control circuitry of the apparatus shown in FIG. 1 to provide smoothing of the heart rate changes by smoothing the changes sensed in vein diameter, which subroutine is inserted between the first step and the second step of the routine or program shown in FIG. 4.

This is done with a subroutine as shown in FIG. 5 which is inserted between STEPS 1 and 2 of the flow clart shown in FIG. 4.

The steps followed in this subroutine are as follows:

STEP 1a. Here $\Delta D$ is computed.

STEPS 1b-1d. These steps define a counting loop for indexing the subscripts of the previously calculated $\Delta D$'s stored in the memory of the microprocessor 14 starting with a count K=0.

At STEP 1d, the question is asked "Does K=N+1?".

STEP 1e. If K=N+1 at STEP 1d, at STEP 1e the sign of $\Delta D_T$ is stored and all the subscripts are decremented by 1. Then the microprocessor 14, or algorithm carried out therein, continues to STEP 2 of the program shown in FIG. 4.

STEP 1f. If K≠N+1 at STEP 1d, at STEP 1f, a determination of the sign of the present $\Delta D$ is made to see if it is equal to that of one of the previous N−1 $\Delta D$'s stored in the memory.

If the answer is yes, the microprocessor/program loops back to STEP 1c to increment the subscript of a previously stored $\Delta D$ for the next comparison.

STEP 1g. If the sign of the present $\Delta D$ is not equal to that of one of the previous N−1 $\Delta D$'s, the sign of the present $\Delta D$ is stored and all stored signs are decremented or moved down one level in the memory stack having a height N−1. Then the microprocessor/program returns to STEP 1a.

From the foregoing description, it will be apparent that the pacing system 10 of the present invention has a number of advantages, some of which have been described above and others of which are inherent in the invention.

In particular, the system 10 can be used solely by itself for controlling pacing rate relative to changes in venous blood vessel diameter Alternatively, the pacing system 10 can be utilized in conjunction with another system for controlling pacing relative to the change of a physiological parameter which changes during exercise but which may change as a result of exercise such that there is a time lag between the need for increased cardiac output as exercise begins and before the change in the physiological parameter is sensed.

See for example U.S. Pat. No. 4,566,456 issued on Jan. 28, 1986 to Gerrit Koning and Edward Schroeppel for: APPARATUS AND METHOD FOR ADJUSTING HEART/PACER RATE RELATIVE TO RIGHT VENTRICULAR SYSTOLIC PRESSURE TO OBTAIN A REQUIRED CARDIAC OUTPUT, U.S. Pat. No. 4,716,887 issued on Jan. 5, 1988 to Gerrit Koning and Edward Schroeppel for APPARATUS AND METHOD FOR ADJUSTING HEART-/PACER RATE RELATIVE TO CARDIAC $pCO_2$ TO OBTAIN A REQUIRED CARDIAC OUTPUT and U.S. Pat. No. 4,768,143 issued on Nov. 24, 1987 to Edward Schroeppel for METHOD FOR CONTROLLING PACING OF A HEART IN RESPONSE TO CHANGES IN STROKE VOLUME the disclosures of which are incorporated herein by reference. In such a system, the sensor for sensing changes in venous blood vessel diameter of the present invention can be added to a lead having another heart function parameter sensor, such as sensor 50 shown in FIG. 1 and a suitable program can be provided for enabling that sensor to initially control changes in pacing rate as the body anticipates the need for exercise. Then such other system can take over the control of adjustment of pacing rate as the physiological parameter sensed by that system changes and such changes are sensed by that system.

The manner in which the sensors 34 and 50 are coupled to the microprocessor 14 in the pacer 12 and utilized by the microprocessor 14 to control pacing of the heart will be readily apparent to those skilled in the art. However, to the extent that further details as to how such control can be effected will be helpful to the understanding and utilization of the method and apparatus of the present invention, reference is made to U.S. Pat. Nos. 4,428,378 and 4,566,456, the disclosures of which are incorporated herein by reference.

The Anderson et al U.S. Pat. No. 4,428,378 and the Koning et al U.S. Pat. No. 4,566,456 each disclose a pacer and a pacing lead with a pacing electrode which is controlled by variation in a human function parameter according to an algorithm and each discloses a microprocessor, a sensor, circuit connections therebetween and circuitry in, or associated with, the microprocessor for carrying out the algorithm to control pacing rate during exercise when the heart is not naturally paced at the rate required during exercise. Anderson et al teaches control of pacing relative to sensed human body mechanical activity and Koning et al teaches control of pacing relative to changes in maximum pressure sensed in a right ventricle.

Also it will be apparent from the foregoing description that modifications can be made to the pacing system 10 of the present invention without departing from the teachings of the present invention. For example, the means for detecting or sensing changes in venous blood vessel diameter could be other than a piezoelectric sensor. For example, an ultrasound sensor or an optical sensor could be utilized for sensing venous blood vessel diameter changes.

Accordingly, the scope of the present invention is only to be limited as necessitated by the accompanying claims.

I claim:

1. An apparatus for pacing a heart in accordance with the heart/pacer rate needed to produce a required cardiac output while a person is exercising, said apparatus acting in response to change in venous blood vessel diameter and comprising:
   a pacer for implantation in a human body and having a pulse generator and control circuitry including a microprocessor for controlling operation of said pulse generator;
   a pacing lead for implantation in a heart having a tip electrode for engaging and supplying pacing pulses to a right ventricle of a heart;
   means for determining changes in diameter of a vein in the human body; and
   said control circuitry including means for relating the changes in venous blood vessel diameter with the required pacing rate needed to supply a desired cardiac output and means for causing said pacer to pace the heart at the required rate when the heart is not naturally paced.

2. The apparatus of claim 1 wherein said means for determining changes in diameter of a vein comprise piezoelectric sensing means.

3. The apparatus of claim 2 wherein said pacing lead comprises a lead body made of insulating material and said piezoelectric sensing means is mounted in the wall of said lead body.

4. The apparatus of claim 3 wherein said piezoelectric sensing means is positioned in said lead body a predetermined distance behind said tip electrode at a position where such sensing means will lie in a vein when the pacing lead is mounted in a heart.

5. The apparatus of claim 1 wherein said microprocessor includes a memory having an algorithm and a lookup table having required pacing rates relative to various values of venous blood vessel diameter stored therein.

6. The apparatus of claim 5 wherein said microprocessor includes:
   means for determining the venous blood vessel diameter at a first point in time;
   means for computing the incremental change in venous blood vessel diameter $\Delta D = D_T - (D_{T-1})$;
   means for looking up the corresponding $\Delta R$ in the look-up table;
   means for computing the required heart rate $R_T = \Delta R + (R_{T-1})$;
   means for determining whether the computed heart rate is equal to or above the programmed maximum pacer rate or is equal to or below the programmed minimum pacer rate; and
   means for replacing the pacer rate $R_{T-1}$ by either the programmed maximum pacer rate or programmed minimum pacer rate stored in the memory of the microprocessor and means for replacing the last sensed D value with the newly sensed D value when the calculated heart rate meets either of the above conditions;
   means for replacing the last pacing rate by the newly computed rate and means for replacing the last venous blood vessel diameter value by the newly determined venous blood vessel diameter when the heart rate calculated is between the maximum and minimum pacer rates stored in the memory of the microprocessor; and
   means for adjusting the pacer rate to the value of the heart rate just calculated.

7. The apparatus of claim 6 including means for smoothing the changes in venous blood vessel diameter.

8. The apparatus of claim 7 wherein said smoothing means includes means for comparing the sign of the result of $\Delta D_T = D_T - (D_{T-1})$ to the sign of the N−1 previously computer differences which have been stored means for determining the appropriate rate changes when there is no sign change in N consecutive samples, means for incrementing to the next $\Delta D$ for the next comparison when the sign of the present increment in diameter D is equal to the sign of the previous N−1 increments in diameter, and means for storing the new sign in the memory when the sign changes.

9. The apparatus of claim 8 including means for basing the rate change on the average value of $\Delta D$ over the N most recent samples if no sign change has occured.

10. A method for pacing a heart in accordance with the heart rate needed to produce a required cardiac output while the person is exercising in response to changes in venous blood vessel diameter, comprising the steps of:

sensing natural pacing of a heart;

determining changes in the diameter of a vein;

relating the changes in venous blood vessel diameter with the required heart rate needed to supply a desired cardiac output; and pacing the heart at the required heart rate when the heart is not naturally paced.

11. The method of claim 10 including the step of sensing venous blood vessel diameter with a piezoelectric pressure sensor.

12. The method of claim 10 wherein said steps of relating venous blood vessel diameter with the required pacing rate comprises the steps of:

determining the diameter of a vein at a point in time T;

looking up the corresponding heart rate change $\Delta R_T$ in a look-up table of heart rates relative to various values of venous blood vessel diameter;

adjusting the pacer rate to the value looked up in the look-up table and monitoring and repeating the step of determining blood vessel diameter and changing the pacing rate as the venous blood vessel diameter changes.

13. The method of claim 10 wherein said step of relating the venous blood vessel diameter with the required heart rate comprises the steps of:

determining the venous blood vessel diameter at a first point in time;

computing the incremental change in venous blood vessel diameter $\Delta D = D_T - (D_{T-1})$;

looking up the corresponding $\Delta R$ in a look-up table of heart rates relative to various values of venous blood vessel diameter;

computing the required heart rate $R_T = \Delta R + (R_{T-1})$;

determining whether the computed heart rate is equal to or above the programmed maximum pacer rate or is equal to or below the programmed minimum pacer rate; and if the calculated heart rate meets either of these conditions, replacing the pacer rate $R_{T-1}$ by either the programmed maximum pacer rate or programmed minimum pacer rate stored in a memory and replacing the last sensed venous blood vessel diameter with the newly sensed venous blood vessel diameter value; or if the heart rate calculated is between the programmed maximum and minimum pacer rates stored in a memory, replacing the last pacing rate by the newly computed rate and replacing the last venous blood vessel diameter value by the newly determined venous blood vessel diameter value; and adjusting the pacer rate to the value of the rate just calculated.

14. The method of claim 13 including the step of smoothing the changes in venous blood vessel diameter to smooth the heart/pacer rate changes.

15. The method of claim 14 including the steps of: comparing the sign of the result, $\Delta D_T = D_T - (D_{T-1})$ to the sign of the $N-1$ previously computed differences which have been stored and if there is no sign chage in N consecutive samples, determining the appropriate rate changes, if the sign of the present increment in venous blood vessel diameter $\Delta D$ is equal to the sign of the previous N-1 increments in venous blood vessel diameter changes, incrementing another increment of venous blood vessel diameter changes $\Delta D$ for the next comparison, and if the sign changes, storing the new sign in the memory and returning to the initial step of determining venous blood vessel diameter.

16. The method of claim 15 including the step of basing the rate change on the average value of $\Delta D$ over the N most recent samples if no sign change has occurred 17. A system for pacing a heart in accordance with the heart/pacer rate needed to produce a required cardiac output while a person is exercising, comprising: a pacer for implantation in a human body and having a pulse generator and control circuitry including a microprocessor for controlling said pulse generator; a pacing lead for implatation in a heart having a tip electrode for engaging and supplying pacing pulses to a right ventricle of a heart; means for determining changes in a heart function parameter; said control circuitry including means for relating the changes in the heart function parameter with the required pacing rate needed to supply desired cardiac output and means for causing said pacer to pace the heart at the required rate when the heart is not naturally paced; means for sensing changes in diameter of a vein in the human body which are anticipatory of the need for an increased cardiac output as a result of emotional stress or the beginning of exercise and for alerting said control circuitry, when the vein diameter decreases, that a higher cardiac output will soon be needed; and means for causing said control circuitry to increase the pacing rate in anticipation of the need for increased cardiac output.

18. A method for pacing a heart in accordance with the heart rate needed to produce a required cardiac output while a person is exercising, comprising the steps of: determining changes in a heart function parameter; determining changes in the diameter of a vein which are anticipatory of the need for an increased cardiac output as a result of emotional stress or the beginning of exercise; causing an increase in pacing rate when the vein diameter decreases to a first higher rate; relating the changes in heart function parameter with the required heart rate needed to supply a desired cardiac output; and pacing the heart at the first higher rate until the rate determined by changes in heart function parameter is the same as said first higher rate; and thereafter controlling the pacing rate relative to changes in the heart function parameter.

* * * * *